(12) United States Patent
Roinestad et al.

(10) Patent No.: US 6,174,497 B1
(45) Date of Patent: Jan. 16, 2001

(54) DETECTION SYSTEMS AND METHODS FOR PREDICTING THE DISSOLUTION CURVE OF A DRUG FROM A PHARMACEUTICAL DOSAGE FORM

(75) Inventors: Kurt Roinestad, Yonkers, NY (US); Frank S. Cheng, Park Ridge, NJ (US); Philip J. Palermo, Bethel, CT (US); Kevin Bynum, Long Island City, NY (US)

(73) Assignee: Euro-Celtique, S.A., Luxembourg (LU)

(*) Notice: Under 35 U.S.C. 154(b), the term of this patent shall be extended for 0 days.

(21) Appl. No.: 08/915,785

(22) Filed: Aug. 21, 1997

Related U.S. Application Data

(63) Continuation of application No. PCT/US97/11791, filed on Jun. 4, 1997.
(60) Provisional application No. 60/018,944, filed on Jun. 4, 1996.

(51) Int. Cl.[7] .................................................... G01N 21/01
(52) U.S. Cl. ..................... 422/82.05; 73/866; 73/866.5; 422/82.01; 422/82.09; 422/82.11; 436/151; 436/164; 436/173; 436/181
(58) Field of Search .............................. 422/82.01, 82.05, 422/82.09, 82.11; 436/151, 164, 173, 181; 73/866, 866.5

(56) References Cited

U.S. PATENT DOCUMENTS

| | | |
|---|---|---|
| 4,335,438 | 6/1982 | Smolen . |
| 5,133,892 | 7/1992 | Chun et al. . |
| 5,142,920 | 9/1992 | Bart et al. . |
| 5,589,649 | 12/1996 | Brinker et al. . |
| 5,638,174 | * 6/1997 | Henderson . |

OTHER PUBLICATIONS

Database CAPLUS, An 1985:172548, Nicklasson et al., Int. J. Pharm., vol. 23, No. 1, pp. 97–108, 1985.*
Database CAPLUS, An 1993:480082, Shivanand et al., Int. J. Pharm., vol. 92, No. 1–3, pp. 35–45, 1993.*
Cho et al. "UV/Visible Spectral Dissolution Monitoring By In–Situ Fiber–Optic Probes"; Anal. Chem. 1995. 67, 2858–2863.

* cited by examiner

Primary Examiner—Jan Ludlow
(74) Attorney, Agent, or Firm—Davidson, Davidson & Kappel, LLC

(57) ABSTRACT

The present invention relates to an improvement in a detection system used for continuously measuring the release of a drug from a pharmaceutical dosage form having a singular dissolution vessel or multiple dissolution vessels containing a dissolution medium and a measuring device for detecting the amount of drug released at a given time, the improvement being a mixing shaft and a probe placed within the mixing shaft or outside the individual dissolution vessels, the probe capable of measuring the dissolution characteristics using UV, IR, near-IR, fluorescence, electrochemical, and Raman spectroscopy techniques. The present invention also relates to a method for predicting the dissolution curve provided by a controlled release pharmaceutical dosage form by taking continuous measurements of the amount of drug released from a dosage form for a portion of the time over which the drug is expected to be released and predicting the remainder of the dissolution curve based on the values obtained.

7 Claims, 13 Drawing Sheets

UV PROBE IN SHAFT
SCALE: 1 UNIT = 1MM

DETECTION SYSTEMS AND METHODS FOR PREDICTING THE DISSOLUTION CURVE OF A DRUG FROM A PHARMACEUTICAL DOSAGE FORM

This application is a continuation of International Application No. PCT/US97/11791, filed Jun. 4, 1997 which claims priority of U.S. Provisional Application Ser. No. 60/018,944, filed Jun. 4, 1996.

BACKGROUND OF THE INVENTION

Dissolution testing is required for all solid oral pharmaceutical solid dosage form forms in which absorption of the drug is necessary for the product to exert the desired therapeutic effect. The U.S. Pharmacopeia (USP) is one well-known standard source of information which provides for dissolution and drug release testing in the majority of monographs for such dosage forms. Exceptions are for tablets meeting a requirement for completeness of solution or for rapid (10 to 15 minutes) disintegration for soluble or radiolabled drugs. The apparatus and procedure conform to the requirements and specificaitons given, e.g., USP 23rd edition Chapter 711 (Dissolution) pages 1791–1793. Dissolution testing serves as a measure of quality control, stability and uniformity as well as a means by which to correlate in-vitro with in-vivo drug release characteristics.

Current USP dissolution methods most commonly employ a temperature programmable water bath, maintained at about 37° C., in which sample vessels are submerged. These vessels contain a predetermined volume of a dissolution media and a means to agitate the contents of the vessel. This may be accomplished by means of a rotating basket attached to a shaft or with a paddle which is also attached to a shaft, both means generally described in USP 23rd edition Chapter 711 (Dissolution) pages 1791–1793. The solid dosage form is placed into the media filled vessel at time zero and specific vessel temperature and mixing speeds are maintained. At fixed time intervals (e.g. 2, 4, 8 hours, etc.) a small aliquot of sample is taken from each vessel, usually by a multi channeled pumping system, and transported to either a cuvette or a sample vial for subsequent spectrophotometric or high pressure liquid chromatography (HPLC) analysis, respectively. Plotting percentage dissolution of a solid dosage form through time results in a dissolution profile.

Of the two methods discussed above, the HPLC method is usually favored over the spectrophotometric method. While HPLC dissolution offers the advantage of specificity, acceptable accuracy, precision and sensitivity, the disadvantage of the status quo rather lies with the inherent burden of creating, manipulating, and storing voluminous numbers of sequence and data files. The cost of TPLC, columns, mobile phases, and the waste solvent disposal, etc., is substantial and the limited number of data points that can be determined may result in a less than ideal representation of the release profile of a solid dosage form over time. Furthermore, HPLC analysis is a sequential time consuming process. In general, a typical 24 hour dissolution requires up to 60 hours to generate a dissolution profile.

Because of the aforementioned disadvantages of currently available systems, an in-situ dissolution method is desirable.

SUMMARY OF THE INVENTION

The present invention relates to an improvement in a detection system used for continuously measuring the release of a drug from a pharmaceutical dosage form comprising a singular dissolution vessel or multiple dissolution vessels containing a dissolution medium and a measuring device for detecting the amount of drug released at a given time, the improvement comprising a mixing shaft and a probe placed within the mixing shaft or outside the individual dissolution vessels, the probe capable of measuring the dissolution characteristics using UV, IR, near-IR, fluorescence, electrochemical, nuclear magnetic resonance (NMR), and Raman spectroscopy techniques.

The present invention also relates to a method for predicting the dissolution curve provided by a controlled release pharmaceutical dosage form comprising taking continuous measurements of the amount of drug released from a dosage form for a portion of the time over which the drug is expected to be released and predicting the remainder of the dissolution curve based on the values obtained.

The present invention relates to a in-situ dissolution methods to evaluate and study the dissolution characteristics of drug formulations. Such methods utilize systems that include fiber optics, ultraviolet spectroscopy, fluorescence spectroscopy, NMR and the like.

The present invention specifically relates to detection systems for measuring dissolution characteristics of pharmaceutical dosage forms using ultraviolet, IR, near-IR, and Raman spectroscopy techniques as well as electrochemical techniques such as polarography, and NMR.

These and other aspects of the present invention can be followed by one skilled in the art by reading the detailed description and the methods provided by the instant invention.

BRIEF DESCRIPTION OF THE DRAWINGS

The following drawings are illustrative of the invention and are not meant to limit the scope of the claims.

DETAILED DESCRIPTION

Figure 1:
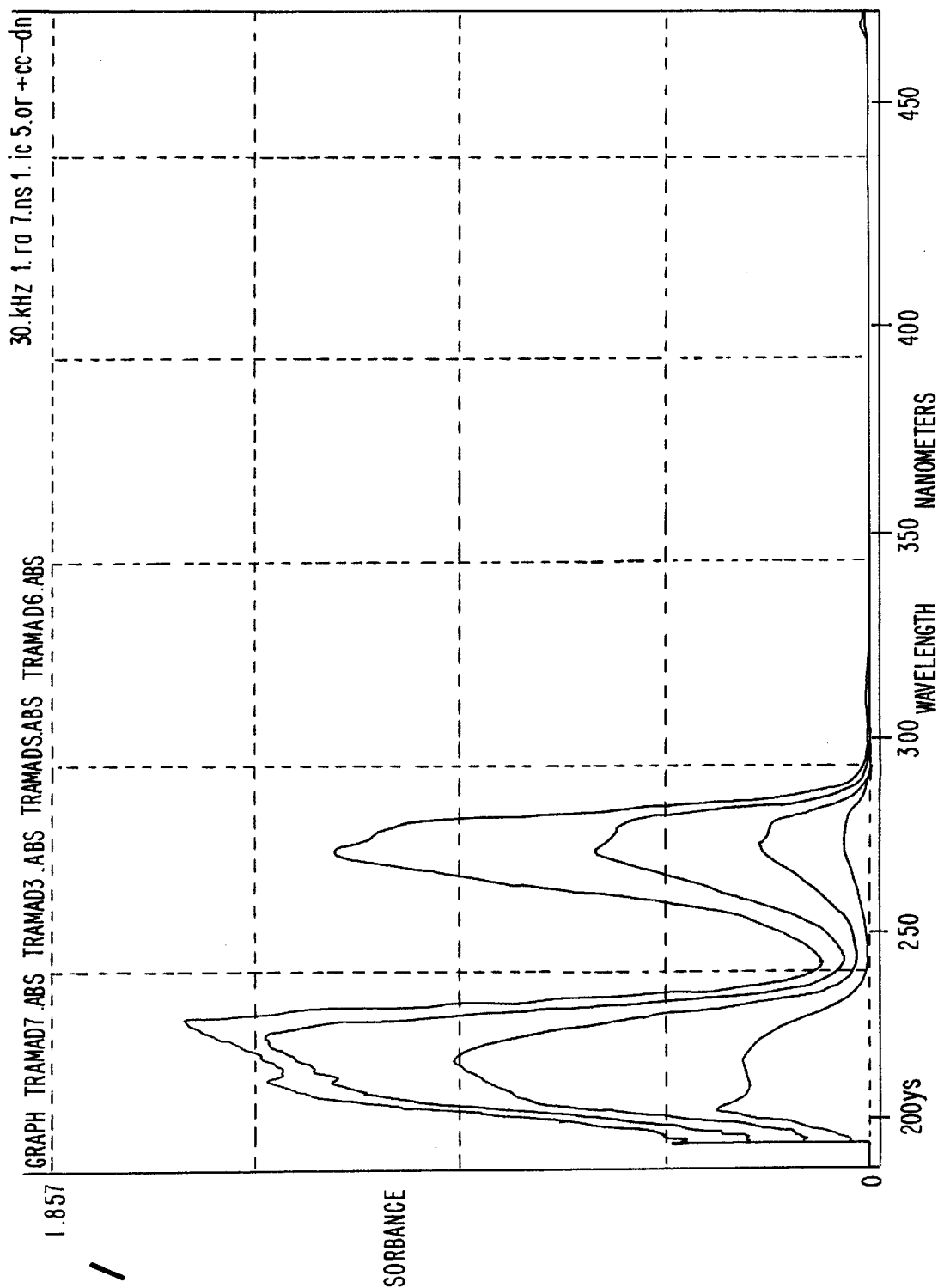
FIG. 1 shows the UV-vis spectra of tramadol standard solutions at four different concentrations.

One aspect of the present invention is related to an improvement in a detection system for continuously measuring the release of a drug from a pharmaceutical dosage form comprising a dissolution vessel containing a dissolution medium and a measuring device for detecting the amount of drug released at a given time, the improvement comprising a mixing shaft having a probe contained within, the probe capable of measuring the release of the drug using fluorescence, ultraviolet (UV), Infrared (IR), near-Infrared (IR), electrochemical, and Raman spectroscopy techniques.

The present invention further provides an improvement wherein the probe utilizes ultraviolet spectroscopy techniques, electrochemical techniques, Infrared (IR), near-Infrared (IR) or Raman spectroscopy techniques.

Another aspect of the present invention provides a method for predicting the dissolution curve provided by a controlled release pharmaceutical dosage form comprising taking continuous measurements of the amount of drug released from a dosage form for a portion of the time over which the drug is expected to be released and predicting the remainder of the dissolution curve based on the values obtained.

A method according to the present invention utilizes a detection system comprising a singular dissolution vessel or multiple dissolution vessels containing a dissolution medium and a measuring device for detecting the amount of drug released at a given time, the improvement in the detection system comprising a mixing shaft and a probe placed within the mixing shaft or outside the individual dissolution vessels, the probe capable of measuring the dissolution characteristics using UV, IR, near-IR, fluorescence, electrochemical, and Raman spectroscopy techniques.

Yet another aspect of the present invention relates to an improvement in a detection system for continuously measuring the release of a drug from a pharmaceutical dosage form comprising a plurality of dissolution vessels containing a dissolution medium and a measuring device for detecting the amount of drug released at a given time, the improvement comprising a mixing shaft having a probe contained within, the probe capable of measuring the release of the drug using fluorescence, ultraviolet, Infrared, near-Infrared, electrochemical, and Raman spectroscopy techniques.

It is further provided that this aspect of the present invention may utilize at least two vessels to optionally hold a dissolution medium or a placebo formulation for baseline correction.

The present invention also provides an improvement in a detection system for continuously measuring the release of a drug from a pharmaceutical dosage form comprising a singular dissolution vessel or multiple dissolution vessels containing a dissolution medium and a measuring device for detecting the amount of drug released at a given time, the improvement comprising a mixing shaft and a probe placed outside the individual dissolution vessels, the probe capable of measuring the dissolution characteristics using UV, IR, near-IR, fluorescence, electrochemical, and Raman spectroscopy techniques.

It is further provided that at least two vessels in the inventive system optionally hold a dissolution medium or a placebo formulation for baseline correction.

The present invention particularly relates to detection systems for measuring dissolution characteristics of pharmaceutical dosage forms using ultraviolet, IR, near-IR, and Raman spectroscopy techniques as well as electrochemical techniques such as polarography.

The present invention also relates to a dissolution apparatus for determining a dissolution profile of a pharmaceutical dosage form containing a releasable quantity of a therapeutically active agent wherein the dosage form is immersed in a dissolution medium contained in a vessel, the apparatus including a detector for quantifying one or more physical and/or chemical properties of the therapeutically active agent, the detector operatively associated with the dissolution medium for at least the time period required for the dosage form to release the maximum releasable quantity of therapeutically active agent; and a data processor for continually processing the generated data for at least the time period required for the dosage form to release the maximum releasable quantity of therapeutically active agent to obtain a dissolution profile of the dosage form.

The present invention also relates to a method for determining a dissolution profile of a pharmaceutical dosage form containing a releasable quantity of a therapeutically active agent wherein the dosage form is immersed in a dissolution medium contained in a vessel, including the steps of continually generating physical and/or chemical data characteristic of the therapeutically active agent by operatively associating a detector with the dissolution medium for at least the time period required for the dosage form to release the maximum releasable quantity of therapeutically active agent; and continually processing the generated data with a data processor for at least the time period required for the dosage form to release the maximum releasable quantity of therapeutically active agent to obtain a dissolution profile of the dosage form.

Another preferred embodiment of the invention relates to a dissolution arrangement for measuring in-vitro release of an active agent from a dosage form containing the active agent, including a plurality of vessels, each of the vessels containing a dissolution media and a dosage form containing an active agent to be measured, a fiberoptic probe associated with each of the vessels, each of the fiberoptic probes including a detector which simultaneously and continuously measures the concentration of active agent in the dissolution media, and a data processor connected to the fiberoptic probes, the data processor continually processing information received from the probes concerning the concentration of the drug to obtain a dissolution profile of the dosage form.

In a more preferred embodiment, the dissolution arrangement further includes utilizing the data processor to predict future concentrations of the active agent. In other preferred embodiments, further include utilizing the data processor to predict the entire dissolution profile of the active agent after at least 50 percent of the entire desired dissolution time frame has elapsed. For example, the dissolution arrangement further comprises utilizing the data processor to predict a 24 hour dissolution profile of the active agent after 16 hours of dissolution time has elapsed.

The term releasable quantity is defined, for purposes of the present invention, as the maximum amount of therapeutically active agent that can be released from a pharmaceutical dosage form during the dissolution testing time period. It will be understood by the skilled artisan that the releasable amount may be less than 100% of the total amount of agent contained in the pharmaceutical dosage form. The dissolution testing time period is preferably at least one hour, and in certain embodiments is 8–24 hours or longer, e.g., 48, 72 or 96 hours.

The term physical and/or chemical properties, for purposes of the present invention, is a physical and/or chemical property that is characteristic of a particular therapeutically active agent. A non-limiting list of physical and/or chemical properties include ultraviolet absorption or radiation spectra; infrared absorption or radiation spectra; α, β or gamma radiation; electron states; polarity; magnetic resonance; concentration electrochemical properties and the like. The physical and/or chemical properties of a agent are any property characteristics of a agent or group of agents that can be used to detect, e.g. the presence, absence, quantity, physical state or chemical state of that agent.

For purposes of the present invention, the term agent is defined as any chemical or physical entity or combination of entities, particles or organisms either that are detectable by a detector. An exemplary list of agents include chemicals, therapeutically active agents, radiation particles (e.g., β-particles); microbes such as bacteria, viruses, individual cells from a multi-cellular organism (e.g., blood cells); and the like.

A detector is defined for purposes of the present invention as any device that detects a physical and/or chemical property of a agent and generate data regarding about the physio-chemical property. Examples of detectors include UV-spectrophotometers, Geiger counters, fluorscopic devices and the like. The physical and/or chemical property detected by the detector and the type of data generated by the detector are not critical to the present invention.

The term "operatively associated" is defined for purposes of the present invention as positioning the detector in proximity to the vessel containing the subject agent such that the detector can quantify the desired physical and/or chemical data characteristic of the agent, and transmit the data to a data processor.

DETAILED DESCRIPTION OF THE INVENTION

The dissolution apparatus of the present invention is particularly useful for determining a dissolution profile of a pharmaceutical dosage form containing a releasable quantity of a therapeutically active agent wherein the dosage form is immersed in a dissolution medium contained in a vessel, the apparatus including a detector for generating physical and/or chemical data characteristic of the therapeutically active agent, said detector operatively associated with the dissolution medium for at least the time period required for the dosage form to release the maximum releasable quantity of therapeutically active agent; and a data processor for continually processing the generated data for at least the time period required for the dosage form to release the maximum releasable quantity of therapeutically active agent to obtain a dissolution profile of the dosage form.

The detector may be any detector known in the art that generates physical and/or chemical data of the test agent, e.g. a uv spectrophotometer. Preferably, the detector has a probe communicably attached thereto. In preferred embodiments, there is at least one detector per sample vessel; i.e. the ratio of detectors to sample vessels is at least 1:1. In other words, for each sample to be analyzed, there is a corresponding detector capable of continuously generating physical and/or chemical data characteristic of the agent to be analyzed.

The data processor may be any device capable of continuously processing the data generated by the detector. In preferred embodiments, the data processor is a computer. The data generated by the detector is preferably stored and/or analyzed by the computer. In a particularly preferred embodiment, the data collector is a computer that has data processing software, e.g. Microsoft Excel 5.0 or Tablecurve. The data generated by the detector is processed by the software and reorganized into a preferred form, e.g. as a graph or a table. The data is preferably continuously processed by the software as it is received from the detector.

In an alternative embodiment, the apparatus further comprises a shaft. The shaft has at least one aperature therein, which aperature allows the detector to detect the necessary physical and/or chemical properties of the subject agent and generate the required physical and/or chemical data. The size and position of the opening along the shaft will depend on a variety of factors, including, but not limited to, the type of detector used and the physical and/or chemical property to be detected.

In preferred embodiments, the shaft has an orifice therein for receiving the detector. When the shaft is received by the connector, it is preferable that the detector is attached to the shaft. In preferred embodiments, the detector is attached to the shaft by any attachment means known in the art, including, but not limited to, welds, adhesives, soldering, screws, friction, and the like.

In a preferred embodiment, the detector is permanently attached to the shaft by, for example, soldering the detector to the shaft. In other preferred embodiments, the detector is rotatably attached to the shaft in a manner such that when the detector is receivedin the shaft, the shaft can freely rotate about the detector, allowing the shaft to perform other functions independent of the detector. For example, a paddle or basket may then be affixed to at least one end of the shaft such when the shaft is rotated, the paddle or basket also rotates to provide, e.g., agitation when the paddle or basket is contacted with an external environment, e.g. dissolution media.

In certain preferred embodiments of the present invention, the detector measures the concentration of the agent, e.g., therapeutically active agent, in the media surrounding the dosage form, e.g., simulated gastic fluid, or simulated intestinal fluid. By measuring the concentration of the agent in the surrounding media, the amount of agent released from the dosage form can be calculated.

The present invention also relates to a method for determining a dissolution profile of a pharmaceutical dosage form containing a releasable quantity of a therapeutically active agent wherein the dosage form is immersed in a dissolution medium contained in a vessel, including the steps of continually generating physical and/or chemical data characteristic of the therapeutically active agent by operatively associating a detector with the dissolution medium for at least the time period required for the dosage form to release the maximum releasable quantity of therapeutically active agent; and continually processing the generated data with a data processor for at least the time period required for the dosage form to release the maximum releasable quantity of therapeutically active agent to obtain a dissolution profile of the dosage form.

In a preferred embodiment, the invention includes three components, a conventional dissolution apparatus, a UV detection unit and a Pentium computer running Windows 95 and Excel 5.0 software. The conventional dissolution apparatus, a Distek 5100 bathless unit (or equivalent unit), is interfaced to a UV radiation source with fiber optic transmission dip probes, and a series of charge coupled detector (CCD) spectrometers which are internalized in the Pentium computer. The computer is configured with Windows 95 and Excel 5.0 for operation of the system and connected to a Novell file server for data storage. Within the Excel software is a template used to run the system. A Dissolution Apparatus is used where vessels are rapidly heated with a thin sheath of electrically resistant material (Distek Premiere 5100 Bathless Unit). A thermocouple present in the shaft of each paddle constantly monitors the temperature of each vessel. The unit uses vessel covers which have been tooled to tightly hold fiber optic probes at specified heights.

Alternatively, a dissolution apparatus utilizing a water bath may be used in place of the bathless unit. A fiber optic dip probe, used for transmission, is interfaced via a sheathed fiber to a deuterium lamp to provide the UV radiation source for the analysis. The dip probe is connected to a CCD spectrometer. Radiation returns from the probe to the CCD spectrometer where it is analyzed and quantitated. Preferably, the internal core of the fiber consists of fused silica, which allows UV radiation to be efficiently propagated. UV radiation is transmitted from the source lamp through the fiber (which extends into the probe) and through a quartz lens seated directly above the flow cell. UV radiation travels through the flow cell and is reflected off a mirror positioned at the terminal end of the probe. The radiation then travels back through the flow cell and quartz lens. It is directed into a second fiber where it travels to the spectrometer for analysis. Quantitation of the drug substance is accomplished by determining the change in intensity of UV radiation as it is transmitted through the flow cell. The spectrometer itself is comprised of a closed optics bench mounted on a printed circuit board which is situated in the computer system. Upon entering the spectrometer, UV radiation is propagated through an optical slit and onto a grating via a mirror. The radiation is then reflected off a second mirror and onto a charge coupled detector. Each fiber optic probe is interfaced to its own spectrometer using universal SMA fittings. The CCD spectrometer is calibrated for both wavelength accuracy and for quantitative accuracy and precision. A second order polynomial equation is used to determine wavelength accuracy. This equation matches each wavelength of light hitting the CCD with a discrete pixel on the array. The control unit is comprised of a Pentium class computer interfaced to the Novell network and fitted with several CCD spectrometers. The spectrometers are entirely controlled through a Microsoft Excel 5.0 template consisting of multiple sheets. Excel communicates with the spectrometers via a device driver library. The system parameters can be adjusted by accessing the data acquisition parameters within the Excel worksheet. The parameters for spectrometer control can be set by using either the mouse or keystrokes. The applicable information such as lot numbers and package types are manually entered into the spreadsheet before the test begins. A worksheet presenting real-time data can then be accessed throughout the dissolution. As the data is collected it is stored on the network.

Generally, the agent is dissolved in the solvent; however, for purposes of the present invention, the agent may be dispersed or suspended throughout the solvent in a solid or semi-solid media. Thus, for purposes of the present invention, the agent need not be dissolved in the solvent, but may, instead, provide a dispersion or suspension medium for the agent.

In a preferred embodiment of the invention the device comprises a detector for monitoring chemical and/or physical properties of an agent, wherein the detector is mounted to a shaft having a hollow portion capable of receiving said detection means, said shaft having an aperature therein that allows said detection means to communicate with said external environment when said detection means is received by said hollow portion. The detection means may be permanently mounted to the shaft, or preferably removably mounted to the shaft to as allow a near infinate combination of shafts and detection means. To facilitate the interchangeabiliy, the mount is preferably a universal mount which will allow an almost infinite combination of detection means and shafts.

In a preferred embodiment, the detection means is capable of aquiring data characteristic of a particular agent by a method selected from the group consisting of ultraviolet radiation, infrared radiation, nuclear magnetic resonance, Raman sprctroscopy, electrochemical, and mixtures thereof, with ultraviolet radiation detection being particularly preferred.

In a particularly preferred embodiment, the shaft is rotatably attached to said detection means, such that the shaft is freely rotatable around the peripheral edges of the detection means when the detection means is situated in the hollow portion of the shaft. In this embodiment, the detection means may or may not be attached in a manner to allow the detection means to independently rotate about an axis within the hollow portion of the shaft, as desired.

In other preferred embodiments of the invention, the device includes a data collecting means, e.g. a computer. In particularly preferred embodiments, the computer is capable of operating data collection software which facilitates analysis or collection of the data generated by the detection means. For example, the software may serve to merely store the data, or it may provide compariitive analysis to rfrence standards, produce graphic representations of the data (e.g., dissolution vs. time curves), or other assorted functions known in the art. The software will preferably be capable of continuously receiving said data from said detection means, providing near-instantaneous access to the data derived from a given test.

The present invention is also directed to a method for continuously monitoring a agent in an external environment, e.g. dissolution media, including the steps of collecting data characteristic to a particular agent in an external environment by positioning at an effective distance to the external environment a device for continually monitoring the agent in the external environment comprising a detection means for detecting a agent in an external environment mounted to a shaft having a hollow portion capable of receiving the detection means; the shaft having an aperature that allows the detection means to communicate with the external environment; and continuously retreiving data obtained from the detection means during the time interval that the device is exposed to the external environment.

It should be understood that the electrochemical techniques used in the present invention optionally include biosensors, in which a transducer is coupled to a biological element, to quantitate a change in concentration of target analyte(s).

DETAILED DESCRIPTION OF PREFERRED EMBODIMENTS

The following examples illustrate various aspects of the present invention. They are not to be construed to limit the claims in any manner whatsoever.

I. Methods

I.1 Material

The new dissolution system has been applied to study the dissolution characteristics of pharmaceutical dosage forms, for example analgesic products, such as Tramadol HCl QD Tablets and Hydromorphone Capsules.

I.2 Apparatus

I.2.1 Fiber Optics/Ultraviolet Spectroscopy

The Ocean Optics Inc. PC Plug-In Fiber Optic Miniature Spectrometer is used with an ultraviolet probe as the method of detection. The probe is coupled to a LS-1 deuterium light source and detection is conducted using a S1000 spectrometer. Data is processed using SpectraScope and Microsoft Excel 5.0 software. The detector is capable of scanning the entire UV and visible spectrum in under 2 seconds. Comparison with the current method for dissolution analysis of solid dosage forms was conducted.

A more powerful deuterium light source from Oriel Corporation, Stratford, CT can also be used to replace the LS-1 deuterium lamp when higher light throughput is required. This light source also has the advantage of using a condensing lens to manipulate the quality of light hitting the fiber optic interface. A xenon arc lamp source from Oriel Corporation may also be used for applications requiring increased sensitivity, such as Hydromorphone and Hydrocodone Controlled Release Products. In addition, a variable path length dip probe from CIC Photonics, Inc. of Albuquerque NM can be used for method development purposes to determine optimal flow cell pathlength for a given drug product.

I.2.2 Fluorescence Spectroscopy

Fluorescence studies were conducted on a Perkin Elmer model LS5 Luminescence Spectrometer. The excitation spectrum was obtained from 220 nm to 500 nm and the emission spectrum was taken from 300 to 800 nm.

I.2.3 Dissolution Apparatus

The dissolution bath was a Hansen Research model SR5 with type II (paddle) agitation. The bath temperature was maintained at 37 +/−0.5 degrees and solution was agitated at 100 rpm.

I.2.4 Software Modules

SpectraScope software from Ocean Optics and Microsoft Excel 5.0 was used for data collection. TableCurve 2D and Table curve 3D from Jandel Scientific Software was used to mathematically model tabulated data and predict experimental results. Disclosure generally describing the above software from Jandel Scientific Software is included under Annexure I, and the same is incorporated herein by reference.

EXAMPLES

Example 1

In-Situ System Using an Ultraviolet-Visible Spectrometer

Figure 2:
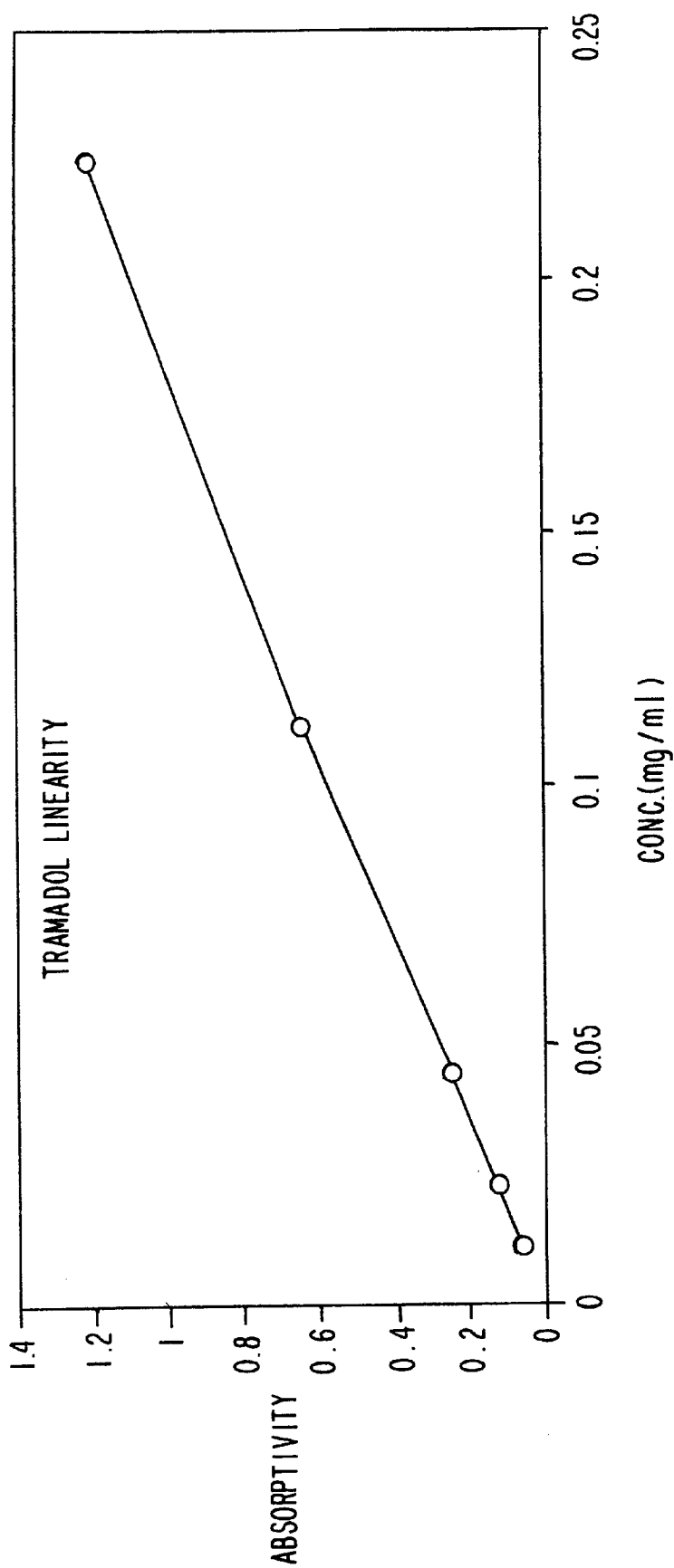
FIG. 2 the linearity plot of tramadol HCl solutions of Example 1.

FIG. 1 shows the UV-vis spectra of Tramadol standard solutions at four different concentrations. Inspection of the spectra in FIG. 1 reveals relatively noise free data with well defined spectral features. The absorbance of Tramadol vs. concentration at the maximum absorbtivity (272 nm) are shown in Table 1 below. The correlation coefficient of the regression line is 0.999825 indicating a linear relationship between concentration and absorption. The linearity plot is shown in FIG. 2.

TABLE 1

Linearity of Tramadol HCl

| Tramadol HCl (mg/mL) | Absorption at 272 nm |
|---|---|
| 0.0112 | 0.058 |
| 0.0224 | 0.119 |
| 0.0447 | 0.246 |
| 0.112 | 0.625 |
| 0.224 | 1.211 |
| Correlation Coefficient(r): | 0.999825 |
| Slope: | 5.4292 |
| y-intercept: | 0.001935 |

This demonstrates the feasibility of using the fiber optical probe as a spectrometer.

Example 2

Figure 3:
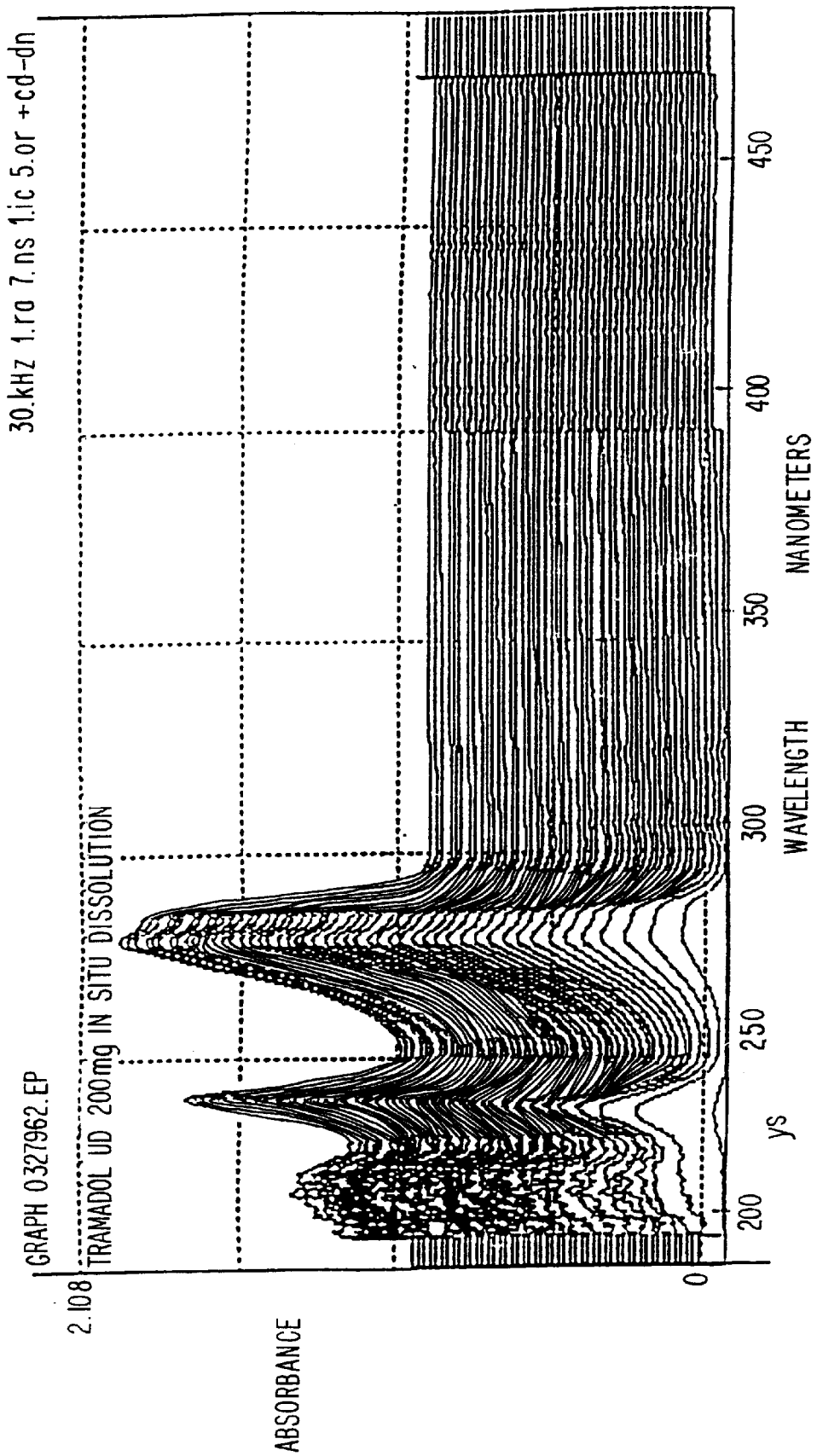
FIG. 3 is a graphical representation of repeated UV-vis scans at 30 minute intervals over 25 hours for a tramadol HCl 200 mg once-a-day tablet of Example 2.

Dissolution of Tramadol 200 mg QD tablets:

Three Tramadol 200 mg QD tablets were placed in the dissolution medium to check its release rate over three different days by the in-situ system. The repeated UV-vis scans at 30 minute intervals over 25 hours for one of the tablets is shown in FIG. 3. The dissolution data of these tablets are shown in Table 2. Table 2 also shows the average of the three and the dissolution results obtained from an existing, validated, HPLC method for comparison.

Figure 4:
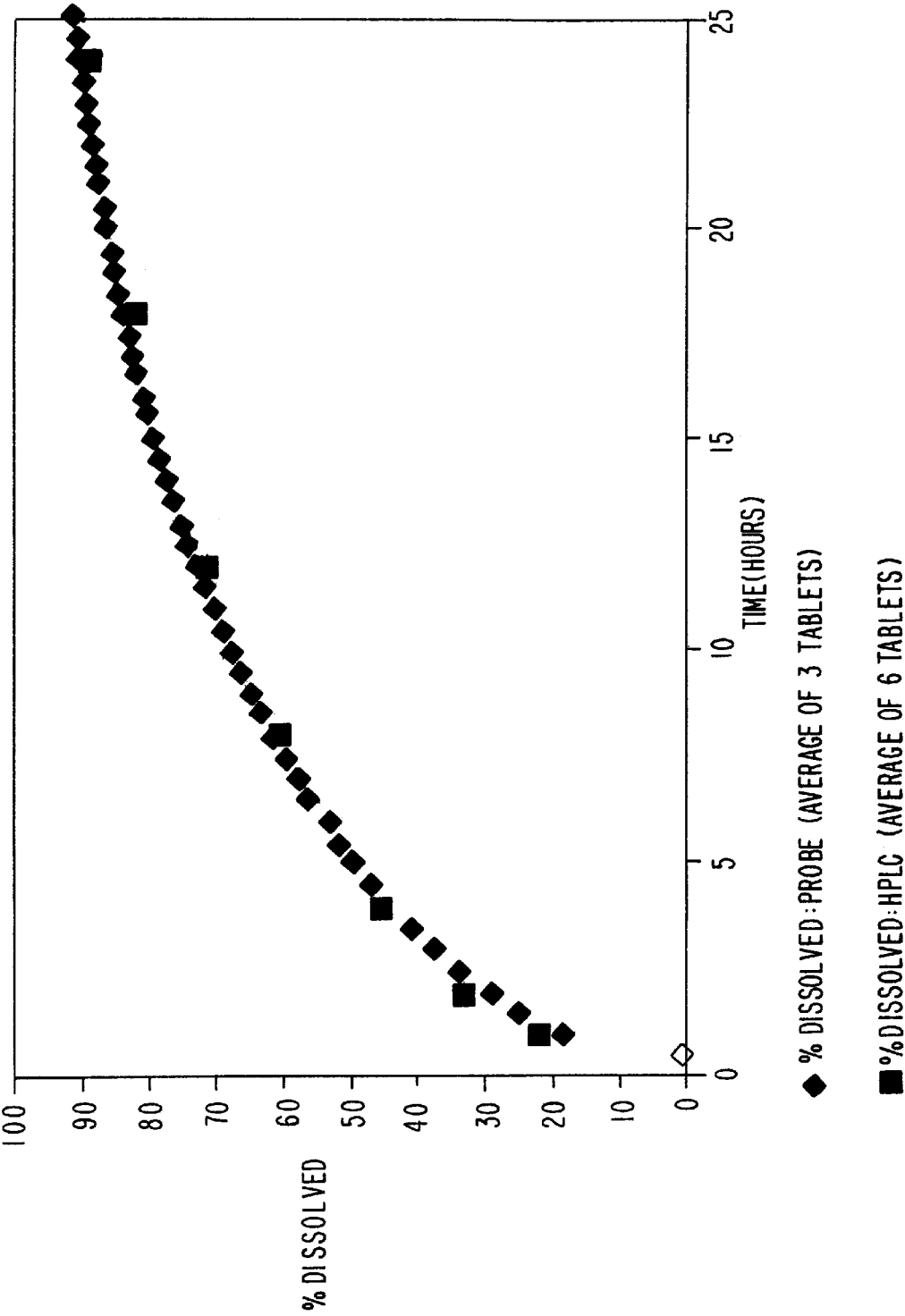
FIG. 4 shows the plot of the average dissolution of three tramadol HCl once-a-day tablets of Example 2 and the results from the HPLC method.

The table clearly demonstrates that the in-situ dissolution system gives results which are precise and correlate well to the current HPLC method. FIG. 4 shows the plot of the average dissolution of three tablets and the results from the HPLC method.

TABLE 2

Dissolution of Tramadol OD 200 mg UV Probe vs. HPLC

| Time (hours) | 4/1/1996 % Dissolved: Probe | 3/29/1996 % Dissolved: Probe | 3/20/1996 % Dissolved: Probe | Average % Dissolved: Probe | % Dissolved: HPLC |
|---|---|---|---|---|---|
| 0.5 | 0 | 0 | 1.8 | 0.6 | ND |
| 1 | 22.8 | 15.4 | 18.2 | 18.8 | 21.8 |
| 1.5 | ND | 23.3 | 27.1 | 25.2 | ND |
| 2 | 27.6 | 28.6 | 30.3 | 28.8 | 32.2 |
| 2.5 | 32.3 | 33.1 | 35.3 | 33.6 | ND |
| 3 | 35.7 | 37.3 | 39.4 | 37.5 | ND |
| 3.5 | 39.2 | 40.1 | 42.9 | 40.7 | ND |
| 4 | 42.0 | 44.0 | 48.0 | 44.0 | 44.7 |
| 4.5 | 45.2 | 46.1 | 48.7 | 46.7 | ND |
| 5 | 47.8 | 46.7 | 51.3 | 49.3 | ND |
| 5.5 | 49.7 | 51.5 | 53.8 | 51.7 | ND |
| 6 | 52.1 | 53.5 | ND | 52.8 | ND |
| 6.5 | 54.1 | 55.1 | 58.3 | 55.8 | ND |
| 7 | 55.9 | 58.7 | 60.4 | 57.7 | ND |
| 7.5 | 57.8 | 58.6 | 62.0 | 59.5 | ND |
| 8 | 59.8 | 60.7 | 63.7 | 61.3 | 60.1 |
| 8.5 | 61.8 | 61.8 | 65.4 | 62.9 | ND |
| 9 | 62.6 | 63.5 | 67.0 | 64.4 | ND |
| 9.5 | 64.8 | 65.1 | 68.3 | 66.1 | ND |
| 10 | 65.7 | 66.4 | 69.7 | 67.3 | ND |
| 10.5 | 68.9 | 67.8 | 70.9 | 68.5 | ND |
| 11 | 68.5 | 68.8 | 72.1 | 69.8 | ND |
| 11.5 | 70.0 | 70.5 | 73.3 | 71.3 | ND |
| 12 | 70.6 | 72.3 | 74.4 | 72.4 | 71.0 |
| 12.5 | 72.4 | 72.8 | 75.7 | 73.6 | ND |
| 13 | 73.4 | 74.1 | 76.7 | 74.7 | ND |
| 13.5 | 74.5 | 75.2 | 76.0 | 75.9 | ND |
| 14 | 75.6 | 75.9 | 79.0 | 76.8 | ND |
| 14.5 | 76.6 | 77.4 | 80.1 | 78.0 | ND |

TABLE 2-continued

Dissolution of Tramadol OD 200 mg
UV Probe vs. HPLC

| Time (hours) | 4/1/1996 % Dissolved: Probe | 3/29/1996 % Dissolved: Probe | 3/20/1996 % Dissolved: Probe | Average % Dissolved: Probe | % Dissolved: HPLC |
|---|---|---|---|---|---|
| 15 | 77.6 | 78.5 | 81.1 | 79.1 | ND |
| 15.5 | 78.3 | 79.4 | 82.2 | 80.0 | ND |
| 16 | 79.2 | 79.1 | 83.1 | 80.5 | ND |
| 16.5 | 79.9 | 80.8 | 84.0 | 81.6 | ND |
| 17 | 80.8 | 81.4 | 84.9 | 82.4 | ND |
| 17.5 | 81.3 | 81.8 | 85.9 | 82.9 | ND |
| 18 | 81.8 | 82.8 | 88.5 | 83.7 | 81.8 |
| 18.5 | 82.7 | 82.8 | 87.2 | 84.2 | ND |
| 19 | 83.3 | 83.9 | 87.9 | 85.0 | ND |
| 19.5 | 84.0 | 84.2 | 88.7 | 85.8 | ND |
| 20 | 84.5 | 84.9 | 89.4 | 86.3 | ND |
| 20.5 | 84.9 | 85.4 | 90.1 | 86.8 | ND |
| 21 | 85.5 | 86.7 | 90.3 | 87.6 | ND |
| 21.5 | 86.2 | 86.5 | 91.4 | 88.0 | ND |
| 22 | 86.4 | 87.5 | 92.0 | 88.6 | ND |
| 22.5 | 87.4 | 88.4 | 92.8 | 89.5 | ND |
| 23 | 88.0 | 88.1 | 93.3 | 89.8 | ND |
| 23.5 | 88.6 | 89.0 | 93.9 | 90.5 | ND |
| 24 | 89.4 | 89.9 | 94.4 | 91.2 | 89.4 |
| 24.5 | 89.3 | 89.6 | 95.1 | 91.3 | ND |
| 25 | 90.3 | 90.5 | 95.5 | 92.1 | ND |

Example 3

Figure 5:
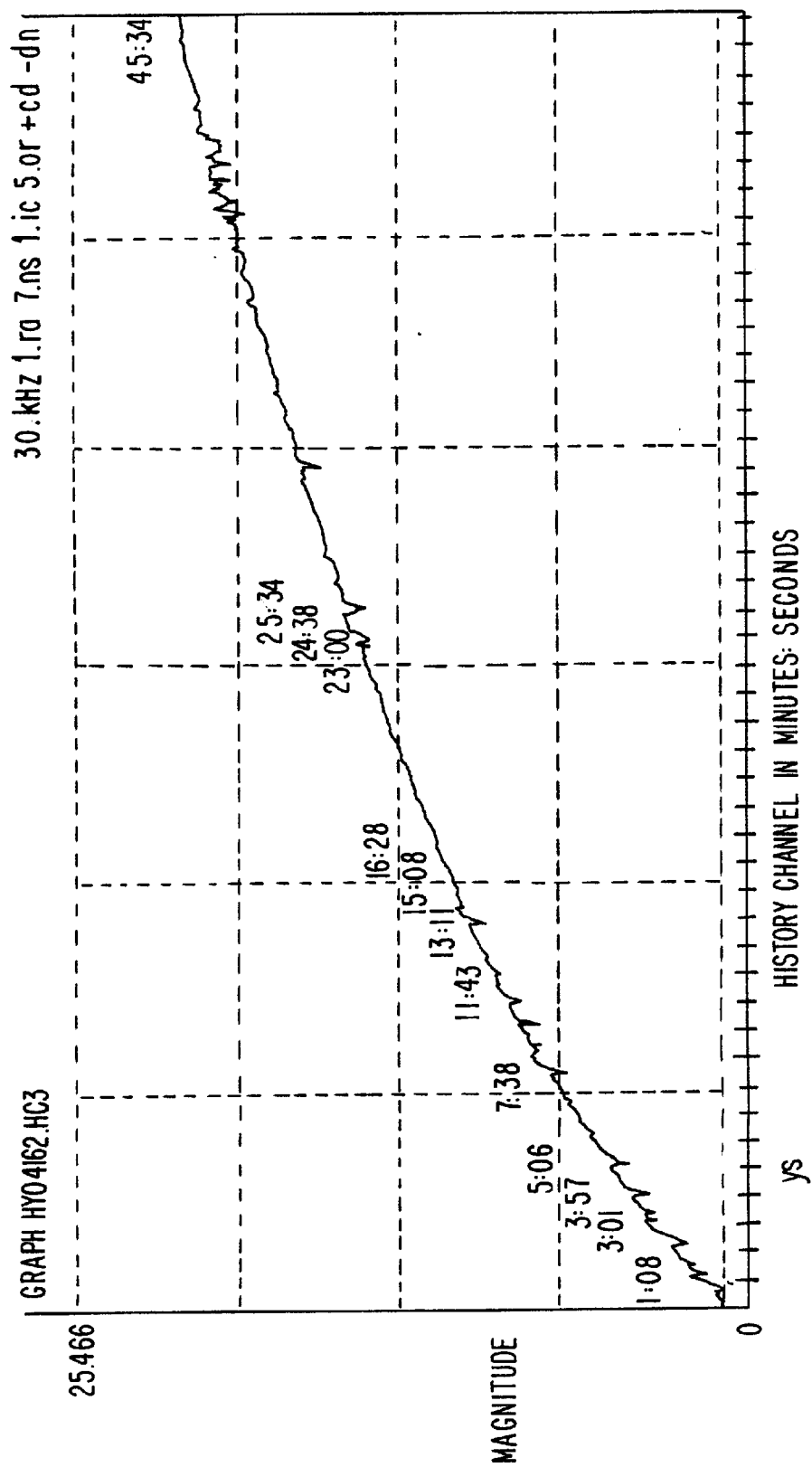
FIG. 5 displays the plot of the dissolution of a tramadol tablet of Example 3 over 45 minutes.

Dissolution profiles generated in real time:

A Tramadol 200 mg QD tablet was placed in the in-situ dissolution system and the amount of Tramadol released monitored in real time. This was obtained by a process called history channel evaluation in which the UV-vis scans of the analyte are acquired in about every 2.5 seconds. The absorption at a pre-selected wavelength is plotted against time to generate a dissolution profile. FIG. 5 displays the plot of the dissolution of Tramadol tablet over 45 minutes. This example illustrates the feasibility of applying the in-situ system to generate the dissolution profile in real time. This is one of the most important applications of the proposed system for immediate release products, because FDA is increasingly requiring for such information.

Example 4

Prediction of the dissolution profile by curve fitting:

Controlled-release pharmaceutical dosage forms in general follow certain release patterns controlled by physical and chemical properties of the matrix. These release patterns can be predicted mathematically.

Figure 6:
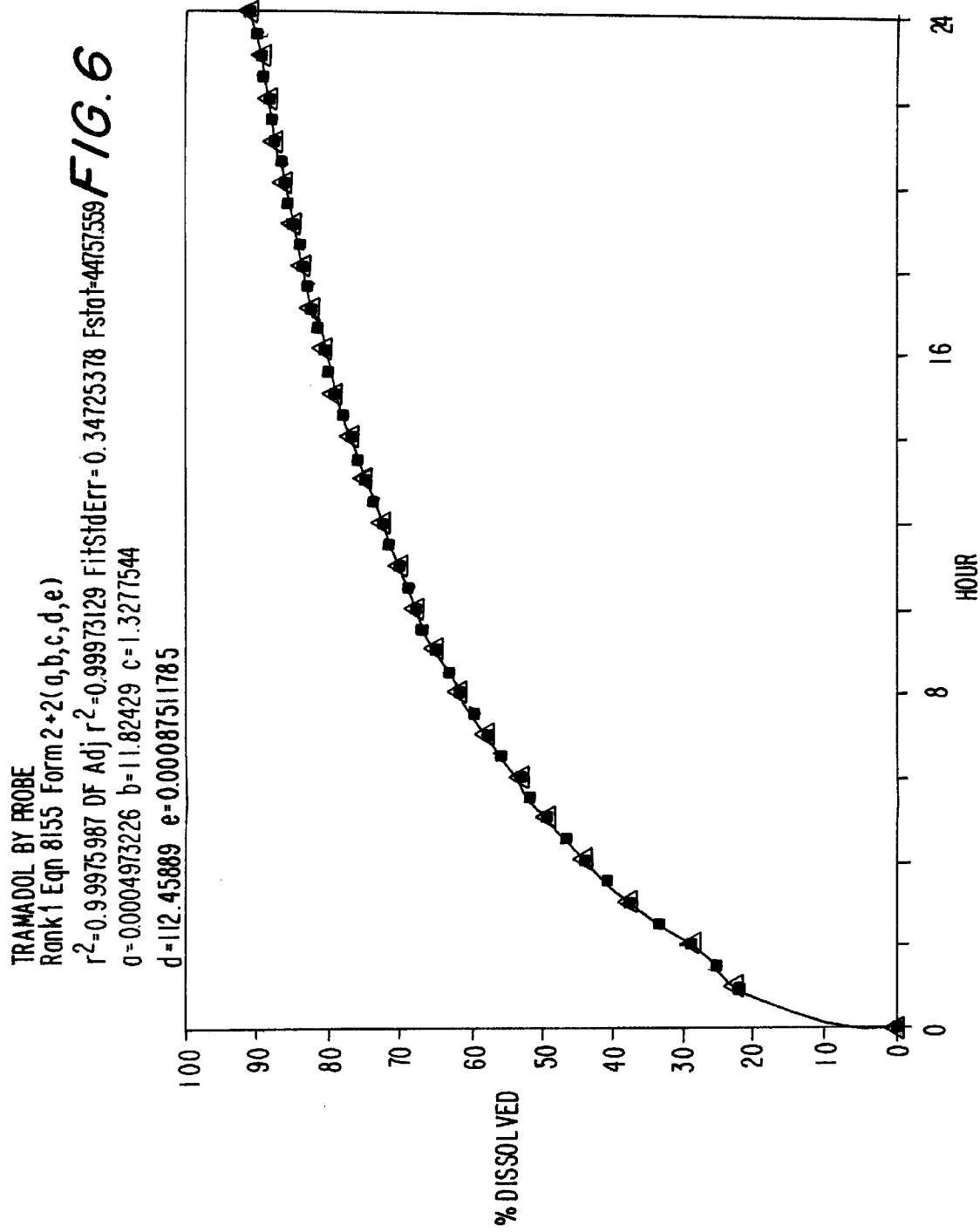
FIG. 6 is a graph of the dissolution profile of a tramadol controlled release tablet, using the average dissolution results from table 1, by using TableCurve 2D program, using the best fit equation (as described in Example 4)

For example, using the average dissolution results from table 1, by using TableCurve 2D program, one can fit the dissolution data into the equation as shown in FIG. 6. On top of FIG. 6, it displays the best-fitted equation for the data.

Figure 7:
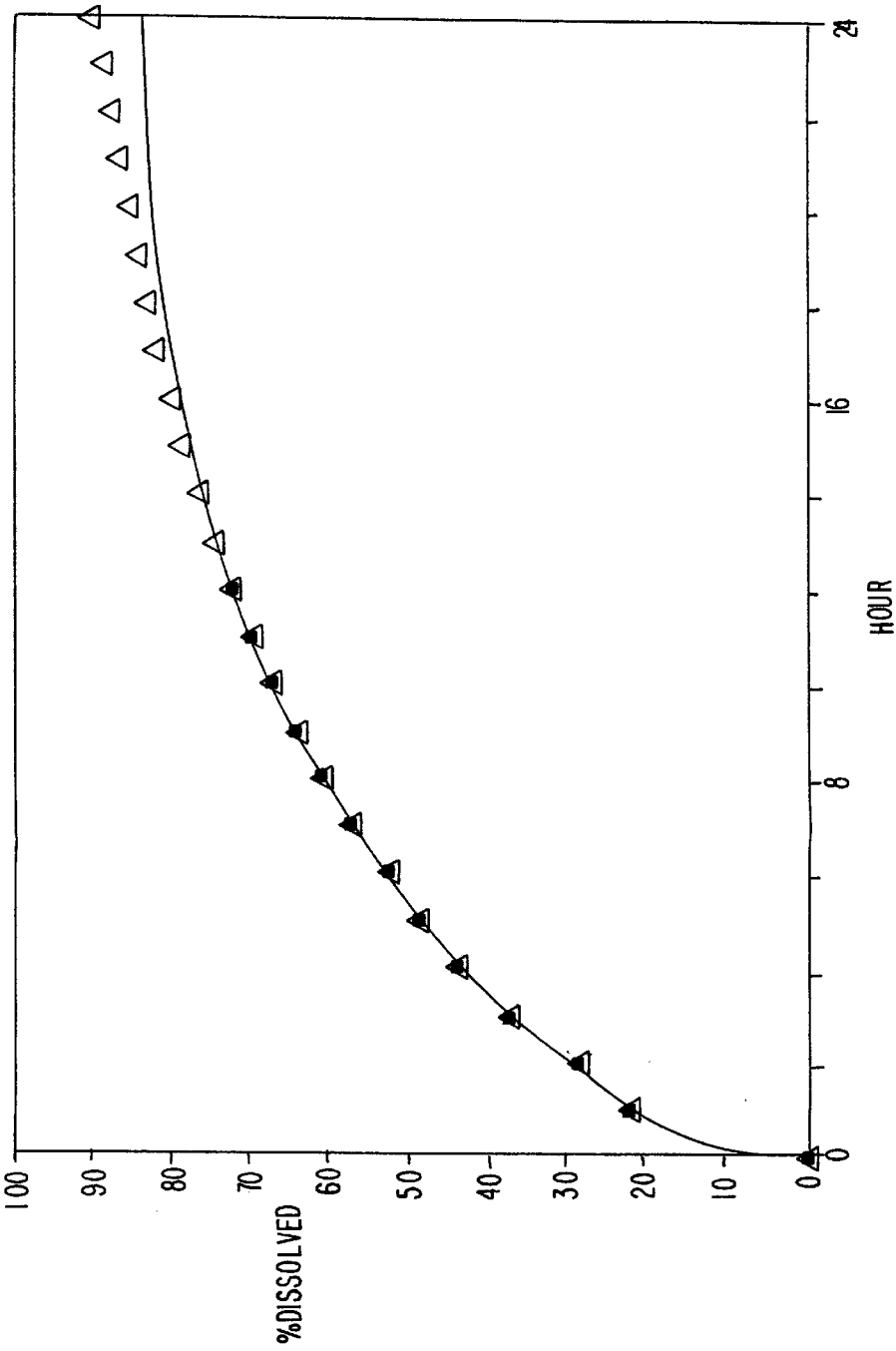
FIG. 7 is a graph showing the dissolution profile of a tramadol controlled release tablet as described in Example 4 obtained from 12 hour sampling data, at 1 hour intervals, using the to the best fit equation (as described in Example 4)
Figure 8:
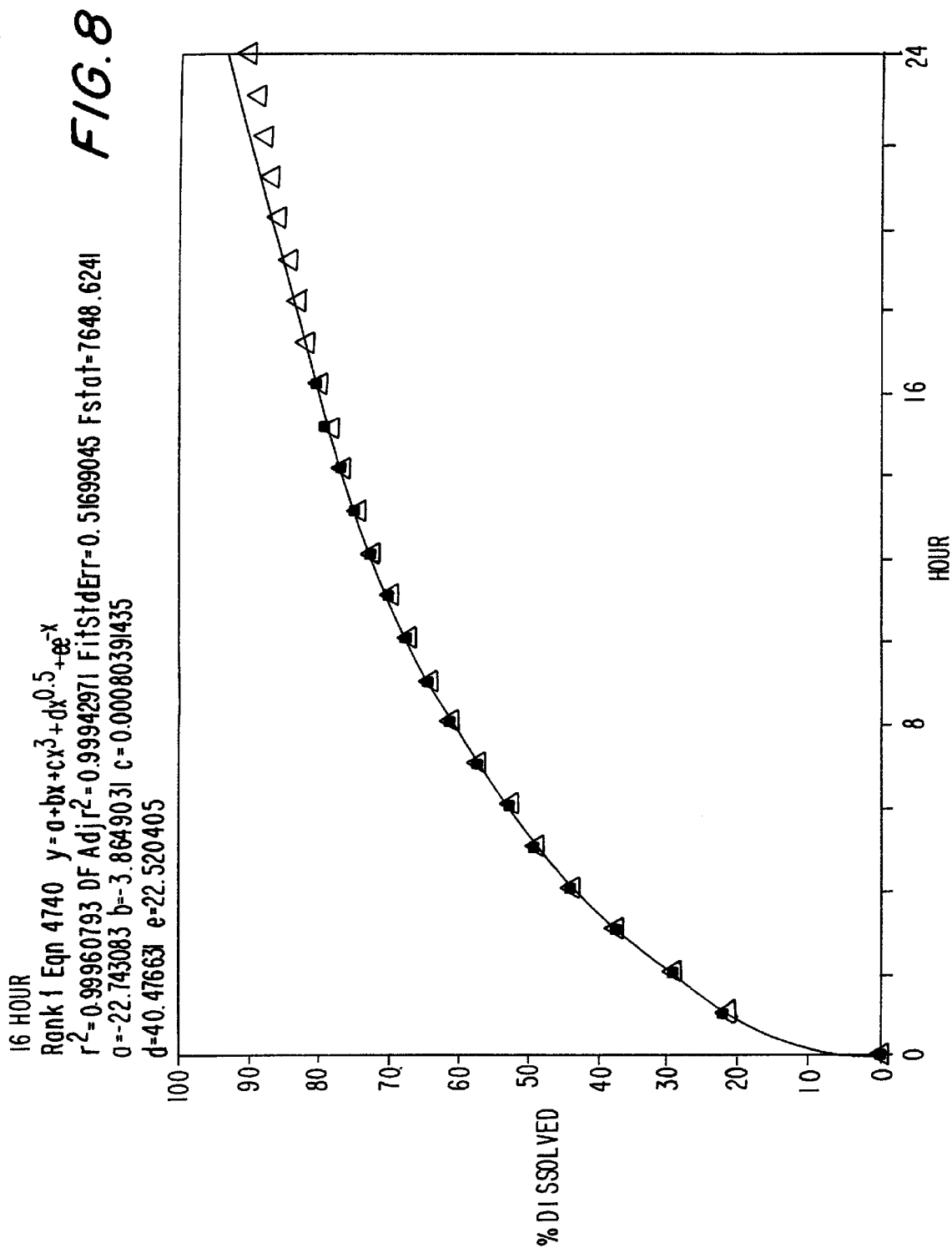
FIG. 8 is a graph showing the dissolution profile of a tramadol controlled release tablet obtained from 16 hour data, taken at 1 hour interval, using the best fitted equation (as described in Example 4)

If one uses the 12 hour data, at 1 hour interval, and fits them to the best fit equation the dissolution profile generate would be as the one shown in FIG. 7. When 16 hour data, taken at 1 hour interval, are taken to find the best fitted equation, it produced the curve of FIG. 8. Note that this curve is closer so that actual experimental data than that generated in FIG. 7.

Figure 9:
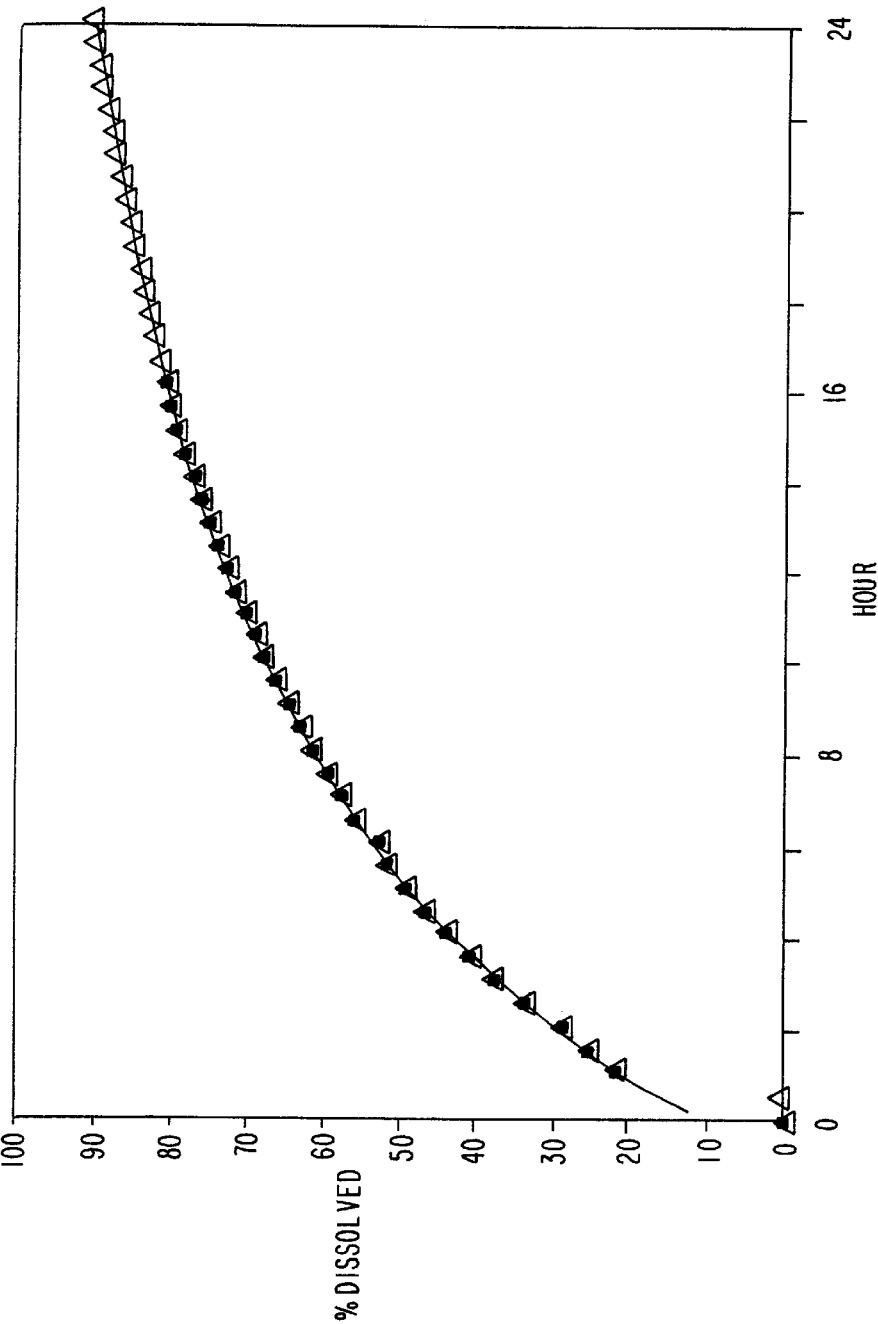
FIG. 9 is a graph of a dissolution profile of a tramadol controlled release tablet, when 16 hour data, generated at every half hour, are used to find the best fit curve (as described in Example 4)

Finally, when 16 hour data, generated at every half hour, are used to find the best fit curve, the equation produced, as shown in FIG. 9, is exactly what one would get in 24 hour experiment, as shown in FIG. 6.

This example clearly demonstrates that it is possible to shorten the experiment by taking more frequent data in a short time and predict the remaining results with mathematical modeling. The in-situ system can work to this purpose because it generates instant data in real time. It is therefore able to give a predicted result to formulators in shorter time.

Example 5

Figure 10:
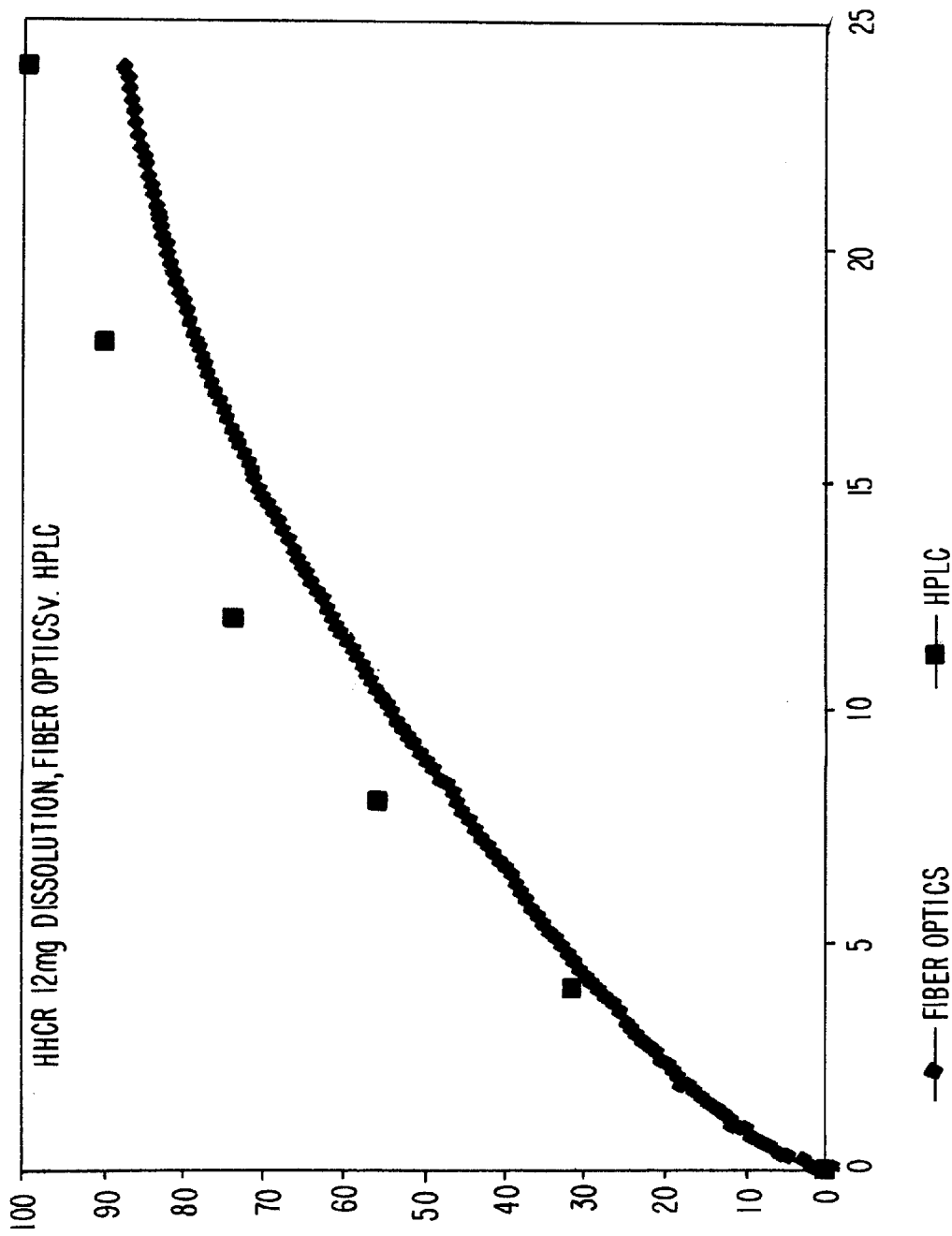
FIG. 10 shows a plot comparison of dissolution data obtained from both a fiber optics v. HPLC methods (as described in Example 6)

Detection of drug products with low dosage strength:

Dissolution testing by conventional spectroscopic methods for low dosage strength products, such as hydromorphone HCl Controlled Release 12 mg capsules, may be difficult due to low concentrations of active drug in the dissolution vessel. Using the combination of a high intensity lamp and a probe tip with a relatively long pathlength (20 mm), a 24 hour dissolution profile has been generated for hydromorphone HCl 12 mg which is comparable to that obtained from a validated HPLC method. Results are displayed in Table 3 and FIG. 10.

TABLE 3

Data of Hydromorphone HCl 12 mg Capsule Dissolution
Fiber Optics v. HPLC

% Hydromorphone HCl Dissolved

| Hour | Fiber | HPLC | Hour | Fiber | HPLC | Hour | Fiber | HPLC | Hour | Fiber | HPLC |
|---|---|---|---|---|---|---|---|---|---|---|---|
| 0 | 1.7 | 0 | | | | | | | | | |
| 0.17 | 2.76 | | 6.17 | 38.9 | | 12.2 | 62 | | 18.17 | 79 | |
| 0.33 | 5.5 | | 6.33 | 39.2 | | 12.3 | 62.5 | | 18.33 | 79.7 | |
| 0.5 | 7.18 | | 6.5 | 40 | | 12.5 | 63.2 | | 18.5 | 79.8 | |
| 0.67 | 8.67 | | 6.67 | 40.6 | | 12.7 | 63.7 | | 18.67 | 80.2 | |
| 0.83 | 10 | | 6.83 | 41.5 | | 12.8 | 64.4 | | 18.83 | 80.5 | |
| 1 | 11.4 | 11.3 | 7 | 42.2 | | 13 | 64.9 | | 19 | 80.8 | |
| 1.17 | 12.5 | | 7.17 | 43 | | 13.2 | 65.5 | | 19.17 | 81.2 | |
| 1.33 | 13.7 | | 7.33 | 43.5 | | 13.3 | 66 | | 19.33 | 81.6 | |
| 1.5 | 14.8 | | 7.5 | 44.2 | | 13.5 | 66.4 | | 19.5 | 82 | |
| 1.67 | 16 | | 7.67 | 44.9 | | 13.7 | 67 | | 19.67 | 82.1 | |
| 1.83 | 17.2 | | 7.83 | 45.7 | | 13.8 | 67.5 | | 19.83 | 82.6 | |
| 2 | 18.1 | 18.2 | 8 | 46.3 | 56 | 14 | 68 | | 20 | 82.9 | |
| 2.17 | 19.3 | | 8.17 | 46.8 | | 14.2 | 68.5 | | 20.17 | 82.9 | |
| 2.33 | 20.1 | | 8.33 | 47.2 | | 14.3 | 69 | | 20.33 | 83.5 | |
| 2.5 | 21.2 | | 8.5 | 48.4 | | 14.5 | 69.6 | | 20.5 | 83.6 | |

TABLE 3-continued

Data of Hydromorphone HCl 12 mg Capsule Dissolution
Fiber Optics v. HPLC

% Hydromorphone HCl Dissolved

| Hour | Fiber | HPLC | Hour | Fiber | HPLC | Hour | Fiber | HPLC | Hour | Fiber | HPLC |
|---|---|---|---|---|---|---|---|---|---|---|---|
| 2.67 | 21.8 | | 8.67 | 49.2 | | 14.7 | 70.2 | | 20.67 | 84 | |
| 2.83 | 22.8 | | 8.83 | 49.6 | | 14.8 | 70.7 | | 20.83 | 84.1 | |
| 3 | 23.8 | | 9 | 50.3 | | 15 | 71.3 | | 21 | 84.4 | |
| 3.17 | 24.7 | | 9.17 | 51.1 | | 15.2 | 71.5 | | 21.17 | 84.6 | |
| 3.33 | 25.4 | | 9.33 | 51.8 | | 15.3 | 72.1 | | 21.33 | 84.9 | |
| 3.5 | 26.1 | | 9.5 | 52.3 | | 15.5 | 72.3 | | 21.5 | 85.2 | |
| 3.67 | 26.9 | | 9.67 | 53.3 | | 15.7 | 72.9 | | 21.67 | 85.4 | |
| 3.83 | 28 | | 9.83 | 53.7 | | 15.8 | 73.4 | | 21.83 | 85.5 | |
| 4 | 28.7 | 31.8 | 10 | 54.4 | | 16 | 73.9 | | 22 | 85.7 | |
| 4.17 | 29.7 | | 10.2 | 55.1 | | 16.2 | 74.3 | | 22.17 | 86.2 | |
| 4.33 | 30.5 | | 10.3 | 55.9 | | 16.3 | 74.8 | | 22.33 | 86.3 | |
| 4.5 | 31.4 | | 10.5 | 56.2 | | 16.5 | 75.3 | | 22.5 | 86.6 | |
| 4.67 | 32.2 | | 10.7 | 57.1 | | 16.7 | 75.6 | | 22.67 | 87.1 | |
| 4.83 | 32.8 | | 10.8 | 57.3 | | 16.8 | 75.8 | | 22.83 | 87.1 | |
| 5 | 33.7 | | 11 | 58 | | 17 | 76.5 | | 23 | 87.1 | |
| 5.17 | 34.4 | | 11.2 | 58.6 | | 17.2 | 76.9 | | 23.17 | 87.3 | |
| 5.33 | 35.3 | | 11.3 | 59.1 | | 17.3 | 77.4 | | 23.33 | 87.5 | |
| 5.5 | 36 | | 11.5 | 59.7 | | 17.5 | 77.9 | | 23.5 | 87.7 | |
| 5.67 | 36.7 | | 11.7 | 60.2 | | 17.7 | 77.9 | | 23.67 | 87.9 | |
| 5.83 | 37.5 | | 11.8 | 60.9 | | 17.8 | 78.4 | | 23.83 | 87.9 | |
| 6 | 38.3 | | 12 | 61.4 | 73.8 | 18 | 78.9 | 90.3 | 24 | 88.3 | 99.8 |

The present invention can also be practiced using techniques and equipment generally described below.

II.1. Detection Systems

II.1.1. Other Fiber Optic Systems

Fluorescence as described in the publication by Glazier, S. A. et al., Analytical Letters (1995) 28, 2607–24, Infrared techniques as described by Krska, R. et al. in Appl. Phys. Lett. (1993) 63, 1868–70, Near IR and Raman techniques as described by Cram, D. J. and Hammond, G. S., Organic Chemistry, McGraw-Hill (1959), all of which are hereby incorporated by reference, either with a grating or interferometer system, are potentially powerful techniques useful for dissolution testing. The techniques can be used with fiber optic spectrometers similar to that of UV. These technologies will be incorporated into the in-situ system similar to that for UV detection.

II.1.2 Electrochemical Detection System

Quantitative electrochemical techniques as described by Cooper, J. C. and Hall, E. A., Journal of Biomedical Engineering, (1988) 10, 210–219, including Differential Pulse Voltametry, Current Polarography and Osteryoung Square Wave Voltametry can be applied to monitor analytes dissolved in dissolution media. These techniques will be used in the in-situ system with different electrode designs, such as platinum or glassy carbon electrodes, for evaluation of different products.

II.1.3. Biosensor

A biosensor, in which a transducer is coupled to a biological element, can be used to quantitate a change in concentration of target analyte as described by Buerk, D. G. in Biosensors: Theory and Applications, Technomic Publishing, (1993), incorporated herein by reference. The biological element can be an enzyme or enzyme system, antigen/antibody, lectin, protein, organelle, cell, or tissue, though enzymes and antigen/antibodies predominate as biological elements of choice, as described by Lowe et al in Journal of Chromatography (1990) 510, 347–354, incorporated herein by reference. The biological element is generally immobilized on a support as described by Coulet et al in Journal of Pharmaceutical and Biomedical Engineering (1988) 10, 210–219, incorporated herein by reference. The transducer may be optic or fiber optic (measuring most commonly changes in absorption or luminescence), or electrochemical. Superior specificity is one of the advantages of biosensors. Such sensors will be used in our systems.

II.2. Probe Design

II.2.1 Probe in Shaft

A distinct configuration, not having been explored in the present art, is the design of a probe which is totally contained in the mixing shaft of each dissolution vessel. The advantage of this system is the absence of flow aberration, since an additional probe need not be submerged in the dissolution media.

II.2.2. Probe Outside of Vessel

An alternate design to the above places probes outside the dissolution vessels. Near IR which has limited interference from the container, such as glass vessel, is good candidate of such detection probe.

III. Temperature Control

The dissolution vessel temperature in the in-situ system can be controlled either by a water bath in which vessels are submerged to maintain appropriate temperature or a bathless configuration, in which each vessel is surrounded by a heating element. The latter configuration reduces the size of the equipment and consequently the bench space, as well as minimizing maintenance. It also allows temperature control of each vessel and also helps to minimize vibration associated with thermocirculation. This is commercially available from Distek, Inc.

IV. System Design

Figure 11:
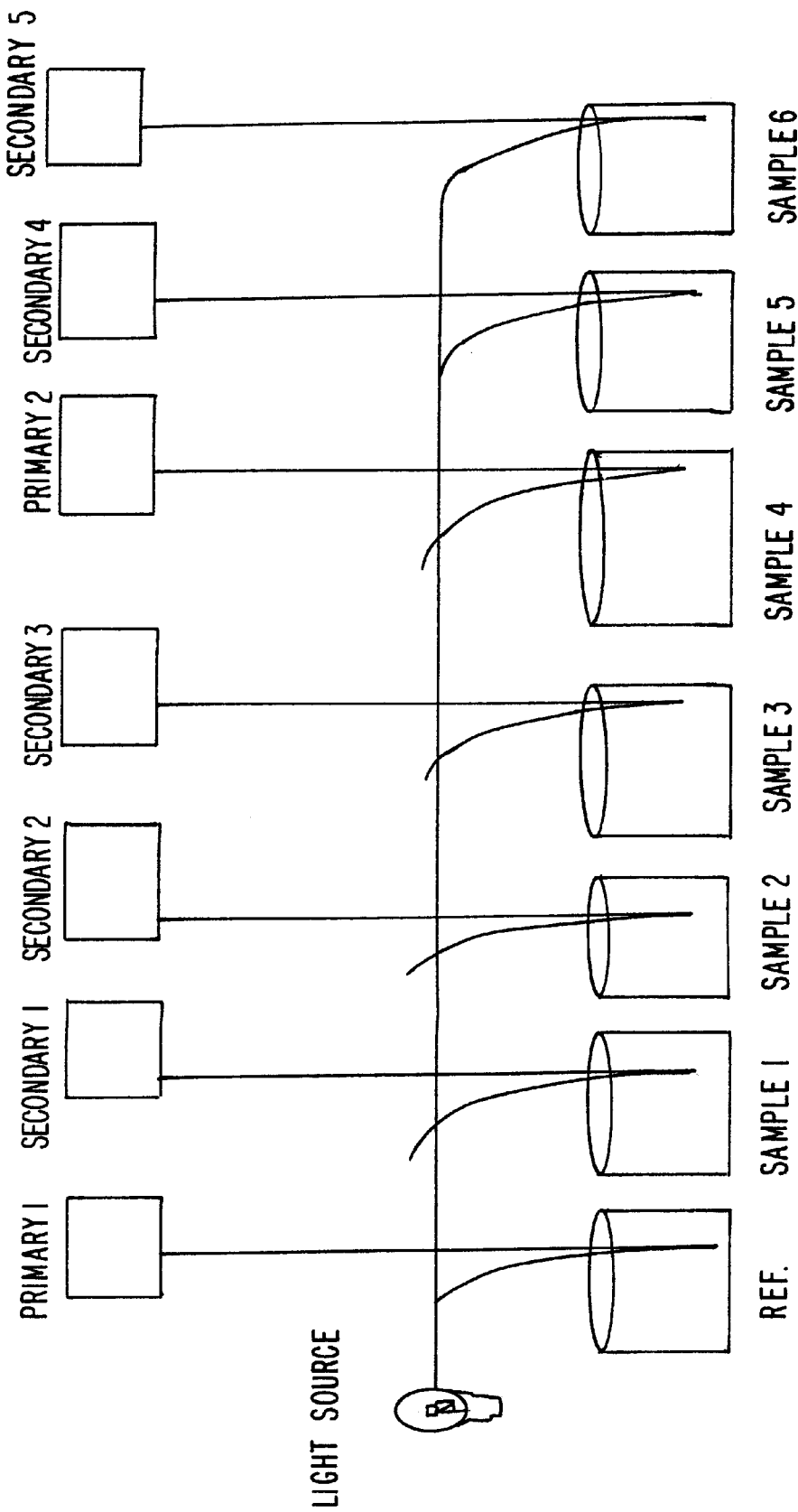
FIG. 11 depicts a preferred configuration of the present invention.

With the above configurations, a system is therefore designed as in FIG. 11. The figure shows seven vessels in which six can be the samples and one for the dissolution medium itself, or a placebo formula for baseline correction. The actual system, of course, can be any number of vessels in the system.

Figure 12:
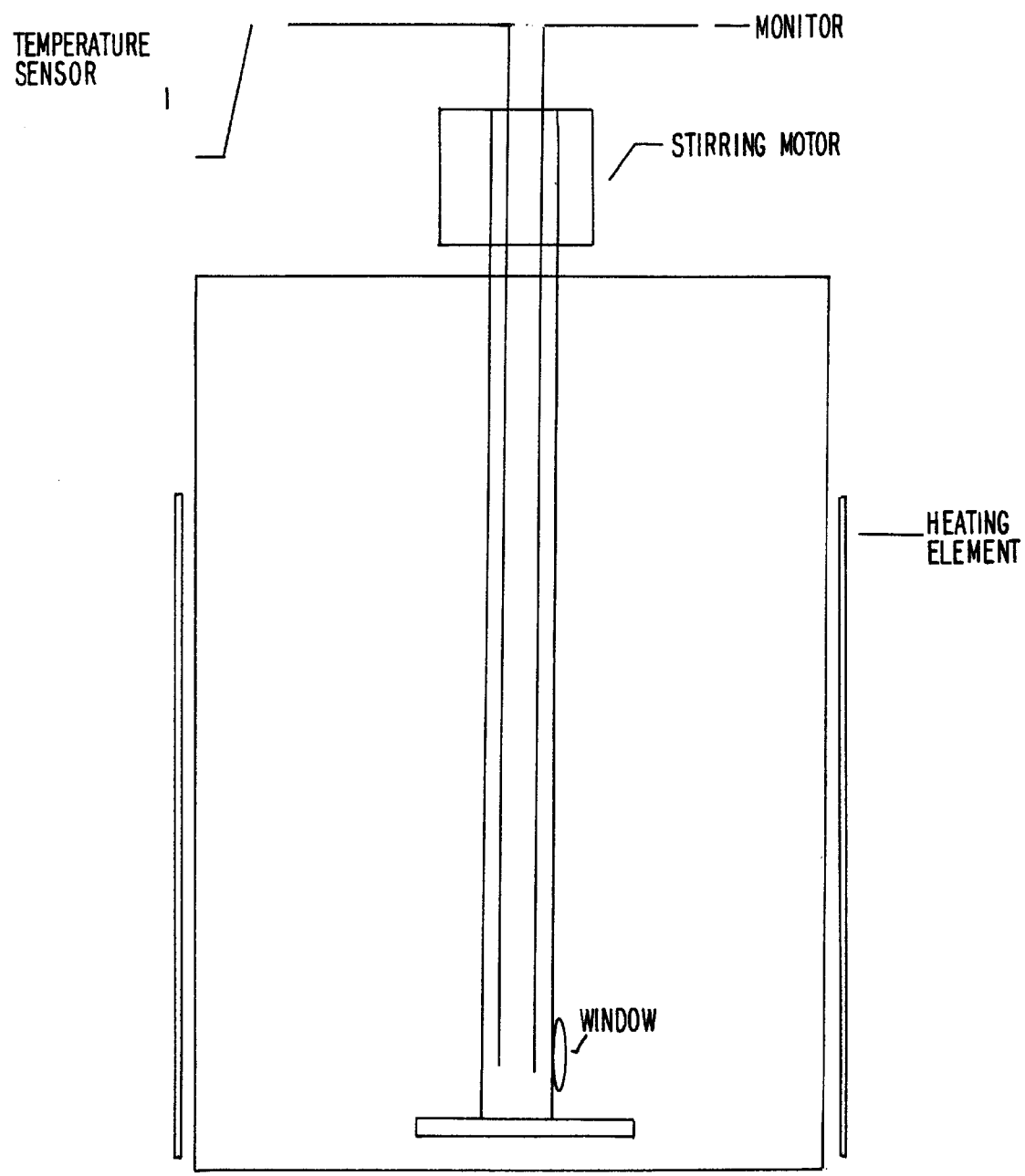
FIG. 12 depicts a closed-vessel embodiment of the invention.
Figure 13:
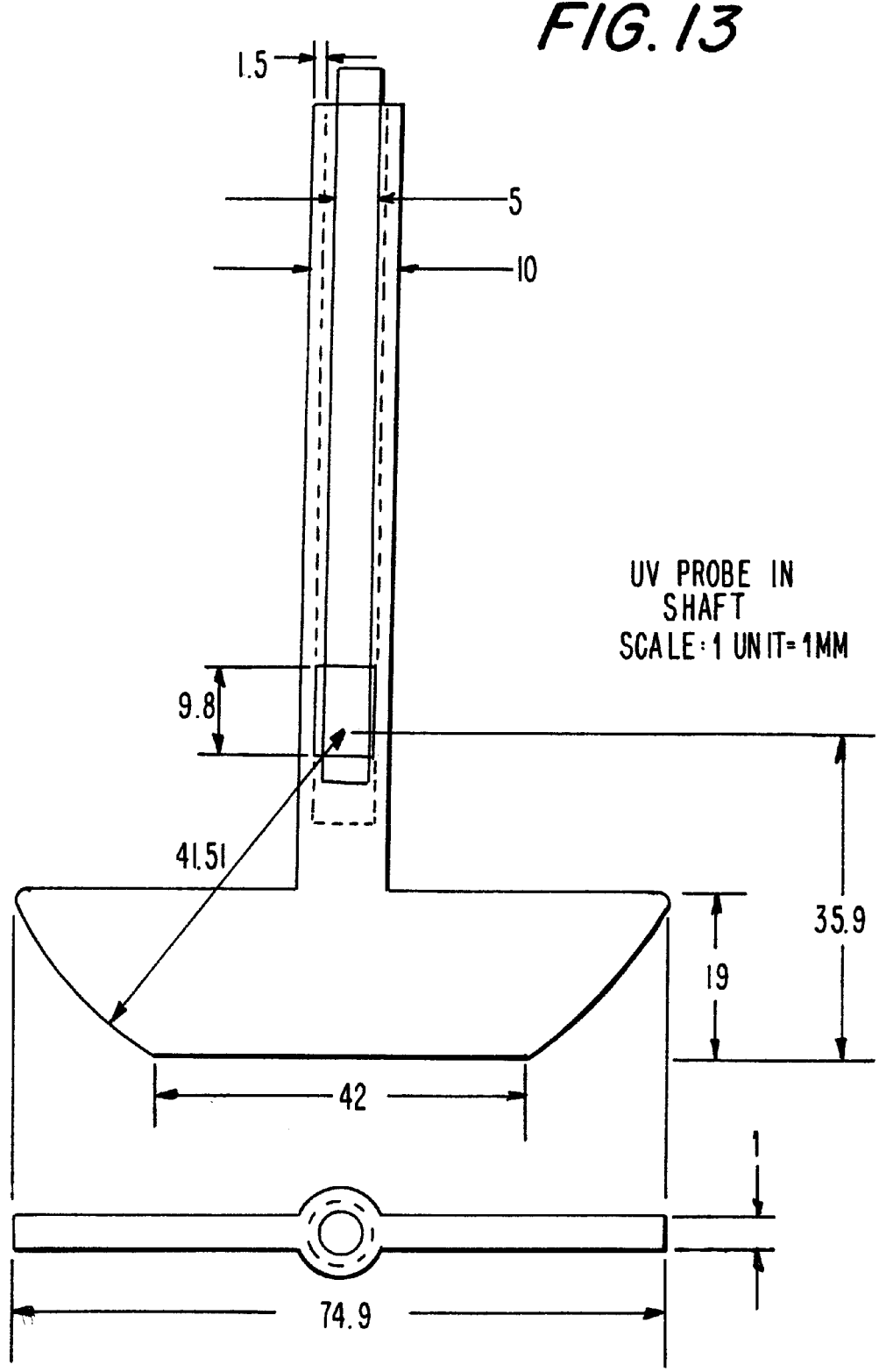
FIG. 13 depicts a UV probe in shaft embodiment of the invention.

This system design may be incorporated with a "closed vessel" design as shown in FIG. 12. The major advantage of this closed design is to minimize loss of dissolution media. FIG. 13 shows a UV probe in shaft embodiment of the present invention.

All of the above-identified references are hereby incorporated by reference. The examples provided above are not meant to be exclusive. Many other variations of the present invention will be readily apparent to those skilled in the art, and are contemplated to be encompassed within the appended claims.

We claim:

1. An apparatus for determining a dissolution profile of a pharmaceutical dosage form containing a releasable quantity of a therapeutically active agent wherein the dosage form is immersed in a dissolution medium contained in a vessel, comprising:

a vessel for immersing a pharmaceutical dosage in a dissolution medium; and a fiber optic probe disposed within a rotatable mixing shaft disposed within the vessel such that the fiber optic probe is operatively associated with the dissolution medium.

2. An apparatus for determining a dissolution profile of a pharmaceutical dosage form containing a releasable quantity of a therapeutically active agent wherein the dosage form is immersed in a dissolution medium contained in a vessel, comprising:

a vessel for immersing a pharmaceutical dosage form in a dissolution medium;

a mixing shaft disposed within the vessel, the mixing shaft being rotatable for agitating the dissolution medium, the mixing shaft having a fiber optic probe contained within, the fiber optic probe being operatively associated with the dissolution medium, a processor coupled to the fiber optic probe, the processor receiving information from the fiber optic probe as the dissolution of the dosage form in the dissolution medium proceeds, the processor analyzing the information and generating a dissolution profile of the dosage form.

3. The apparatus of claim 2, wherein the mixing shaft has a hollow portion for receiving the fiber optic probe, the mixing shaft further having an aperture formed therein for allowing the fiber optic probe to communicate with the dissolution medium.

4. The apparatus of claim 2, wherein the processor includes a computer and a UV-spectrometer.

5. The apparatus of claim 2, wherein the processor continuously receives information from the fiber optic probe as the dissolution of the dosage form in the dissolution medium proceeds, and wherein the processor analyzes the information and continuously generates a dissolution profile of the dosage form as the dissolution of the dosage form in the dissolution medium proceeds.

6. The apparatus of claim 2, wherein the apparatus includes a plurality vessels, each vessel having a respective fiber optic probe disposed therein, and wherein the processor includes a computer coupled to a plurality of UV spectrometers, each fiber optic probe being coupled to a respective one of the UV spectrometers.

7. The apparatus of claim 6, wherein the processor continuously receiving information from the fiber optic probe as the dissolution of the dosage form in the dissolution medium proceeds, the processor analyzing the information and continuously generating a dissolution profile of the dosage form as the dissolution of the dosage form in the dissolution medium proceeds.

* * * * *